United States Patent [19]
Ellingson

[11] Patent Number: 5,697,781
[45] Date of Patent: Dec. 16, 1997

[54] FUNCTIONAL REGULATING DEVICE AND METHOD FOR TREATING MALOCCLUSION

[76] Inventor: Bernhard H. Ellingson, 1545 Riverside Dr., Brainerd, Minn. 56401

[21] Appl. No.: 480,273

[22] Filed: Jun. 7, 1995

[51] Int. Cl.⁶ .................................................. A61C 3/00
[52] U.S. Cl. .................................. 433/18; 433/19; 433/24
[58] Field of Search ............................. 433/18, 19, 24, 433/6

[56] References Cited

U.S. PATENT DOCUMENTS

| | | |
|---|---|---|
| 3,997,970 | 12/1976 | Hodgson . |
| 4,472,138 | 9/1984 | Howe ........................... 433/19 |
| 4,472,139 | 9/1984 | Rosenberg ................... 433/19 |
| 4,708,646 | 11/1987 | Jasper .......................... 433/19 |
| 4,969,822 | 11/1990 | Summer ....................... 433/19 |
| 4,975,052 | 12/1990 | Spencer et al. .............. 433/21 |
| 5,011,404 | 4/1991 | Losi .............................. 433/19 |
| 5,022,855 | 6/1991 | Jeckel .......................... 433/18 |
| 5,057,012 | 10/1991 | Kesling ........................ 433/17 |
| 5,064,370 | 11/1991 | Jones ........................... 433/21 |
| 5,092,768 | 3/1992 | Korn ............................ 433/18 |
| 5,288,229 | 2/1994 | Huff et al. ................... 433/17 |
| 5,299,935 | 4/1994 | Lokar ........................... 433/18 |
| 5,352,116 | 10/1994 | West ............................. 433/19 |

FOREIGN PATENT DOCUMENTS

| | | | |
|---|---|---|---|
| 1079955 | 12/1954 | France | 433/19 |
| 1252156 | 12/1960 | France | 433/19 |
| 2385381 | 10/1978 | France | 433/19 |
| 1183094 | 10/1985 | U.S.S.R. | 433/19 |

OTHER PUBLICATIONS

Howe, Raymond P., *The Herbst Appliance*, copyright 1983.
*The Evolution of Some "Functionals"*.
Howe, Raymond P. and McNamara, James A. Jr., *The Frankel Appliance*, copyright 1983.
Howe, Raymond P., *The Herbst Appliance*, copyright 1983.

Primary Examiner—Nicholas D. Lucchesi
Attorney, Agent, or Firm—Merchant, Gould, Smith, Edell, Welter & Schmidt, P.A.

[57] ABSTRACT

Functional regulating device for adjusting a bite of a jaw having an upper row of teeth and a lower row of teeth is provided. The functional regulating device includes a lower jaw splint constructed and arranged to fit onto the lower row of teeth and be detachable therefrom; an anchor constructed and arranged to attach to the upper row of teeth and be detachable therefrom; and first and second opposed adjustable length connector bars. Each connector bar has a first end and a second end and a predetermined fixed length and non-telescoping action when inserted into a jaw. The first ends of the connector bars are permanently connectable to the lower jaw splint, and the second ends of the connector bars are permanently connectable to the anchor. Additionally provided is a method for treating malocclusion in a patient.

16 Claims, 5 Drawing Sheets

FUNCTIONAL REGULATING DEVICE AND METHOD FOR TREATING MALOCCLUSION

FIELD OF THE INVENTION

The present invention relates to a functional regulating device and to a method for treating malocclusion such as overjet, and more particularly to a functional regulating device which is detachable from a patient's mouth and can be easily reattached without the assistance of a health care professional.

BACKGROUND OF THE INVENTION

Mandibular retrognathia or lower jaw retrusion is a common condition where a patient's lower jaw bites too far back behind the upper jaw, or where a patient's upper row of teeth lies abnormally forward of the lower row of teeth in the jaw. This condition is sometimes referred to as malocclusion or overjet, and is a type of class II relationship.

Functional regulating devices have been used to treat malocclusion or overjet by gradually adjusting the bite over time. It is believed that these devices function by pressuring the lower jaw forward to accelerate its growth. By pushing the lower jaw forward, bone remodeling can occur over time so that the lower jaw development is brought into balance with the development of the upper jaw. Accordingly, it is generally desirable to use these devices on children whose jaws are in the process of developing and can be more easily adjusted. This usually corresponds with children ages 8–12.

Modern functional regulating devices were first introduced in the early 1900's by Dr. Herbst and have been referred to Herbst devices. A Herbst device which is commonly used today is described in *The Herbst*, by Raymond P. Howe, D.D.S., M. S., Partner's Press, Inc., 1983. The device can be permanent or detachable. Generally, however, it is permanently attached to a patient's upper and lower jaw. The device has a sliding or telescoping pin and tube arrangement which holds the upper and lower jaw in position relative to each other. The telescoping pin and tube arrangement includes a lower plunger which slides in and out of an upper sleeve as the mouth opens and closes. In order to increase the length of the telescoping pin and tube arrangements, it is necessary to take the device apart and add washers to the sleeves. The washers restrict the depth the plungers can descend into the sleeves. Unfortunately, such adjustments can be very time consuming, and the removal of the device can cause breakage. Furthermore, it has been found that the pin and tube have a tendency to separate when the patient opens his/her mouth too wide. The patient then has to put the pin and tube back together. For some children, this can be difficult. In addition, this problem is even greater when the Herbst device is detachable from the upper and lower jaw since it separates into two pieces.

The Herbst device has been modified in several ways over the years. For example, U.S. Pat. No. 4,708,646 to Jasper describes a functional regulating device having a flexible member attached to opposite ends of the upper and lower jaw of a patient. The end attachments provide a swiveling action for ease in cleaning the teeth, talking, and chewing. U.S. Pat. No. 4,472,138 to Howe describes a Herbst device which has been modified for use on pre- and early adolescent children not having a full set of permanent teeth. U.S. Pat. Nos. 3,798,773 to Northcutt and 4,551,095 to Mason describe a system of rigid telescoping tubes attached to the archwires of braces. The attachment to the archwire are relatively complicated in order to provide for limited movement. Unfortunately, the links exert excessive forces at their attachment points which can cause problems.

The modified Herbst devices are similar to the Herbst device since they are generally not removable by the patient. In order to function properly, they are generally permanently installed in a patient's mouth and can only be removed by a dentist. The permanency of these devices, however, can have undesirable effects with respect to hygiene and appearance. Since the devices are permanent, cleaning the mouth is more difficult, which can ultimately result in more cavities. Furthermore, it is sometimes desirable to remove the functional regulating device for certain occasions. Accordingly, it would be desirable to provide a functional regulating device which can be conveniently removed and replaced by the patient.

SUMMARY OF THE INVENTION

A functional regulating device for adjusting the bite in a jaw having an upper row of teeth and a lower row of teeth is provided by the present invention. The functional regulating device includes a lower jaw splint constructed and arranged to fit onto the lower row of teeth and be detachable therefrom; an anchor constructed and arranged to attach to the upper row of teeth and be detachable therefrom; and first and second opposed adjustable length connector bars. Each connector bar has a first end and a second end and is constructed and arranged to provide a predetermined fixed length and non-telescoping action when inserted into a jaw as a part of the functional regulating device. The first ends of the connector bars are permanently connectable to the lower jaw splint, and the second ends of the connector bars are permanently connectable to the anchor to provide a hinge action. Preferably, when the functional regulating device is inserted into a patient's jaw, it will provide a hinge action during normal biting motions, and while talking.

The first connector bar is constructed and arranged for placement on the right side of the jaw, and the second connector bar is constructed and arranged for placement on the left side of the jaw. The connector bars are preferably pin and tube arrangements which are crimpable to provide predetermined fixed lengths and non-telescoping rigid members, or rigid wires having an adjustment loop to provide predetermined fixed lengths. It is generally desirable for the connector bars to be capable of adjustment by a doctor while being worn.

The anchor of the functional regulating device can include a lip bumper and/or a pin arrangement constructed and arranged to fit in permanently attached molar bands or headgear tubes. Alternatively, the anchor can include a retainer. The anchor is detachable by the patient and can be re-applied without the assistance of a doctor.

A method for treating malocclusion in a patient is provided by the present invention. The method includes the step of applying a functional regulating device to a patient suffering from malocclusion. The functional regulating device can include a lower jaw splint constructed and arranged to fit onto the lower row of teeth and to be detachable therefrom; an anchor constructed and arranged to attach to the upper row of teeth and to be detachable therefrom; and first and second opposed adjustable length connector bars. The method can additionally include a step of adjusting the length of the connector bars while the patient is wearing the functional regulating device.

3

Figure 1:
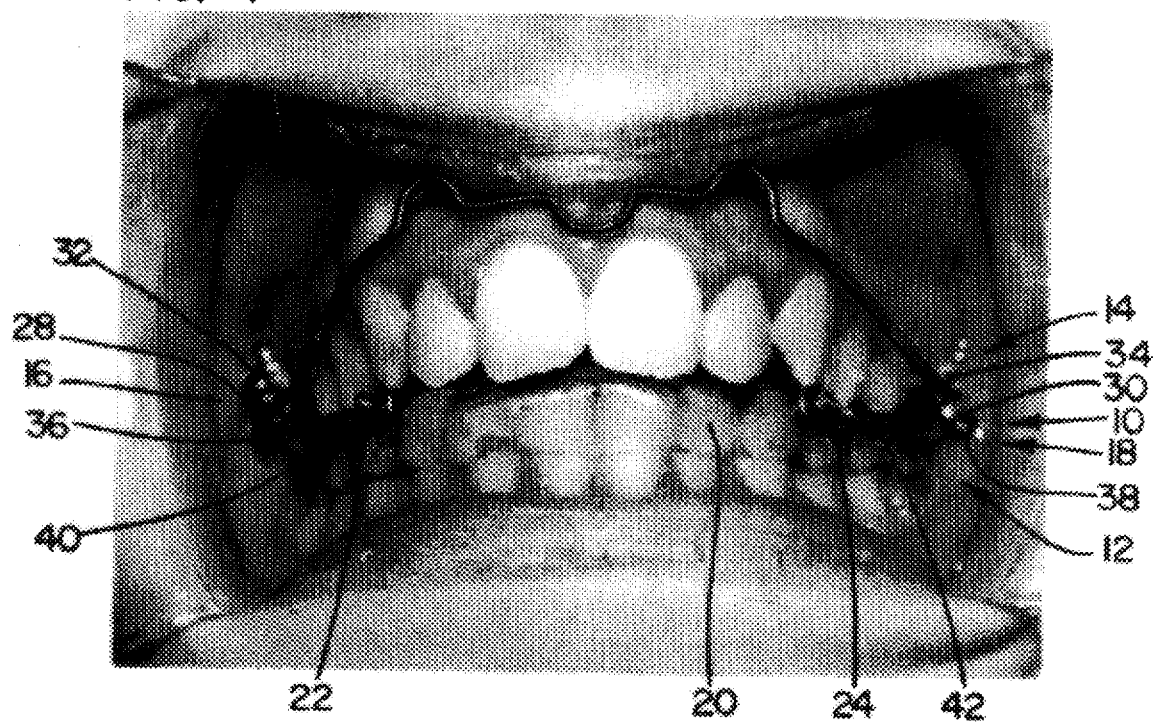
FIG. 1 is a frontal view of a functional regulating device in a patient's jaw according to the principles of the present invention.
Figure 2:
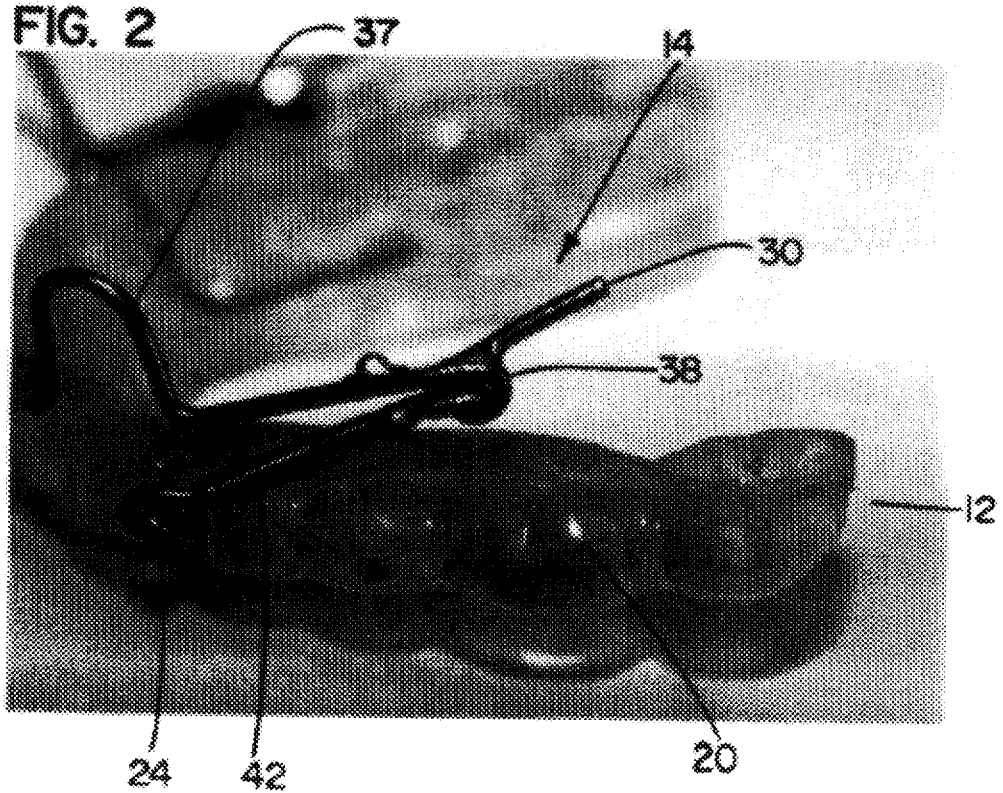
Figure 3:
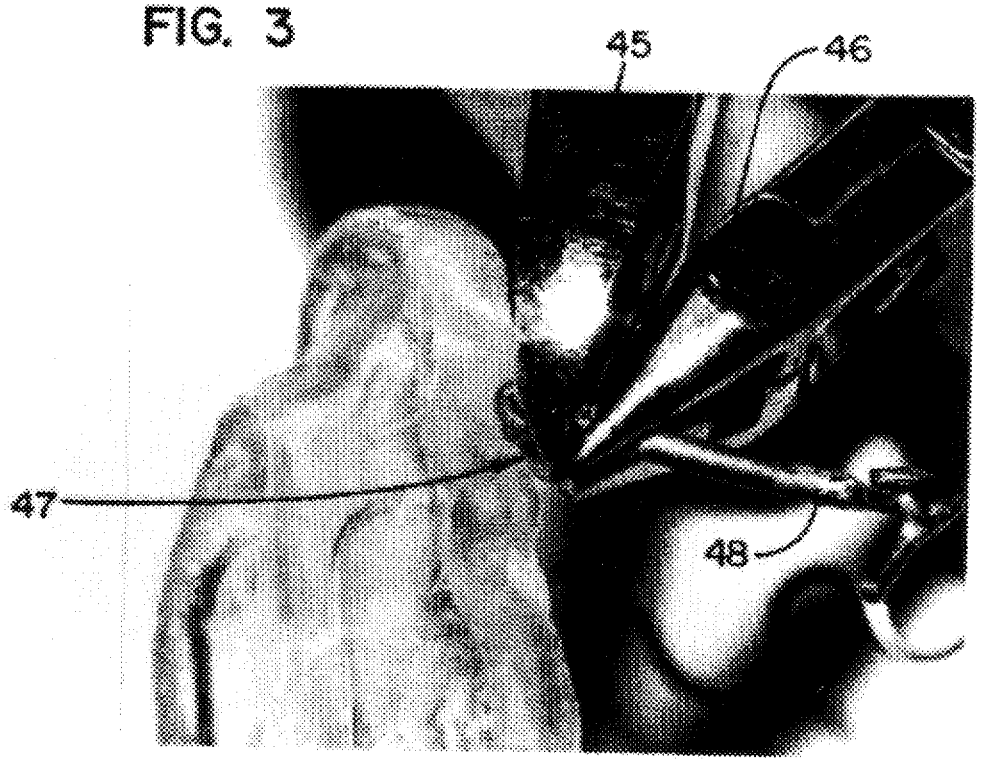
Figure 4:
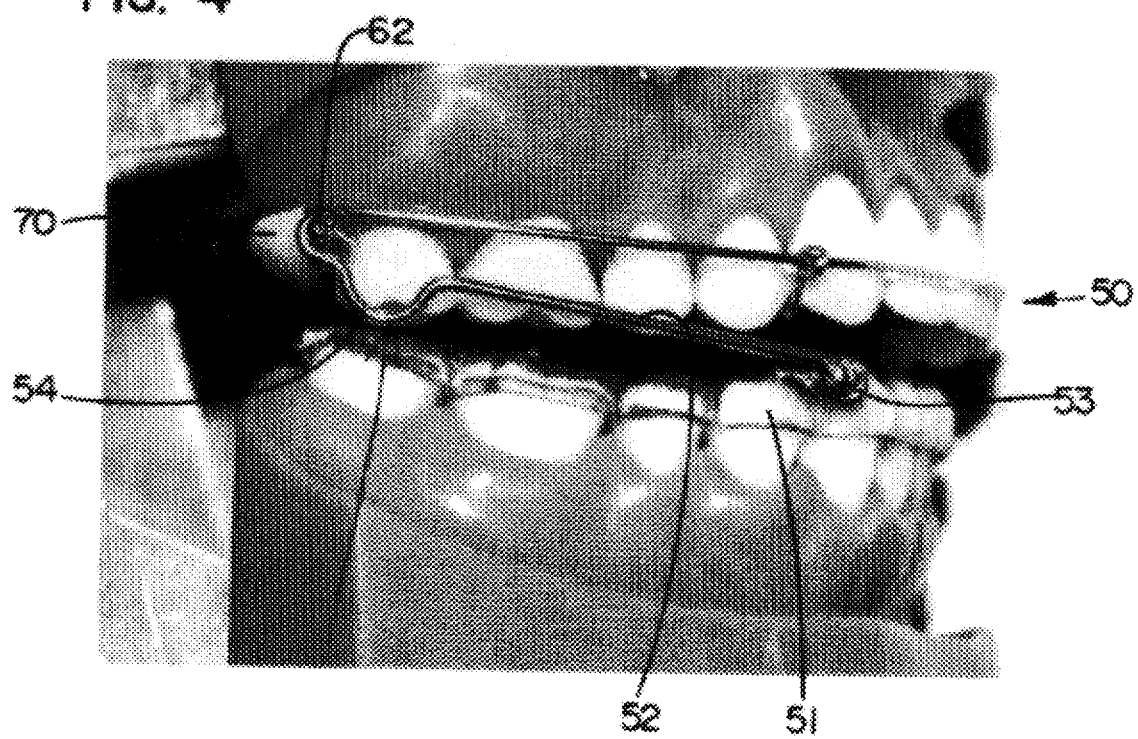
Figure 5:
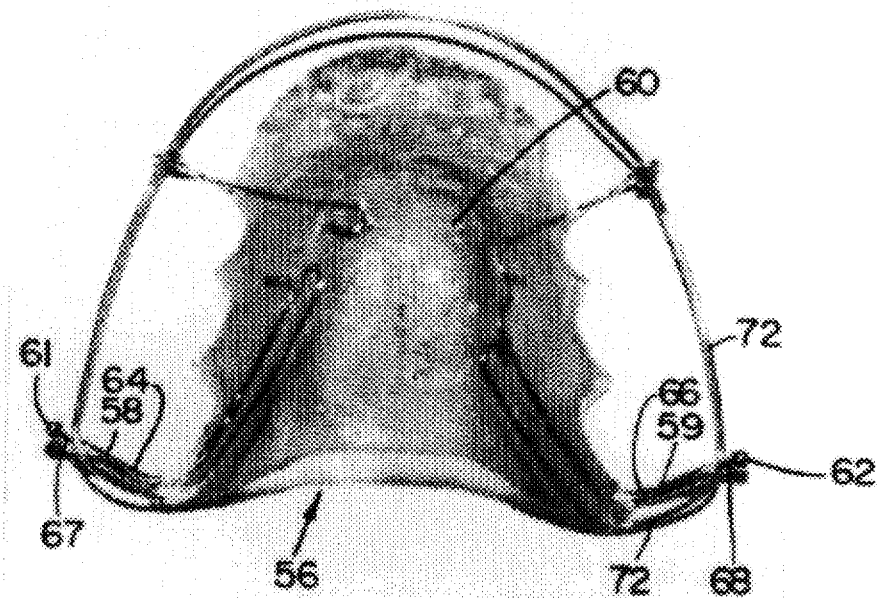
Figure 6:
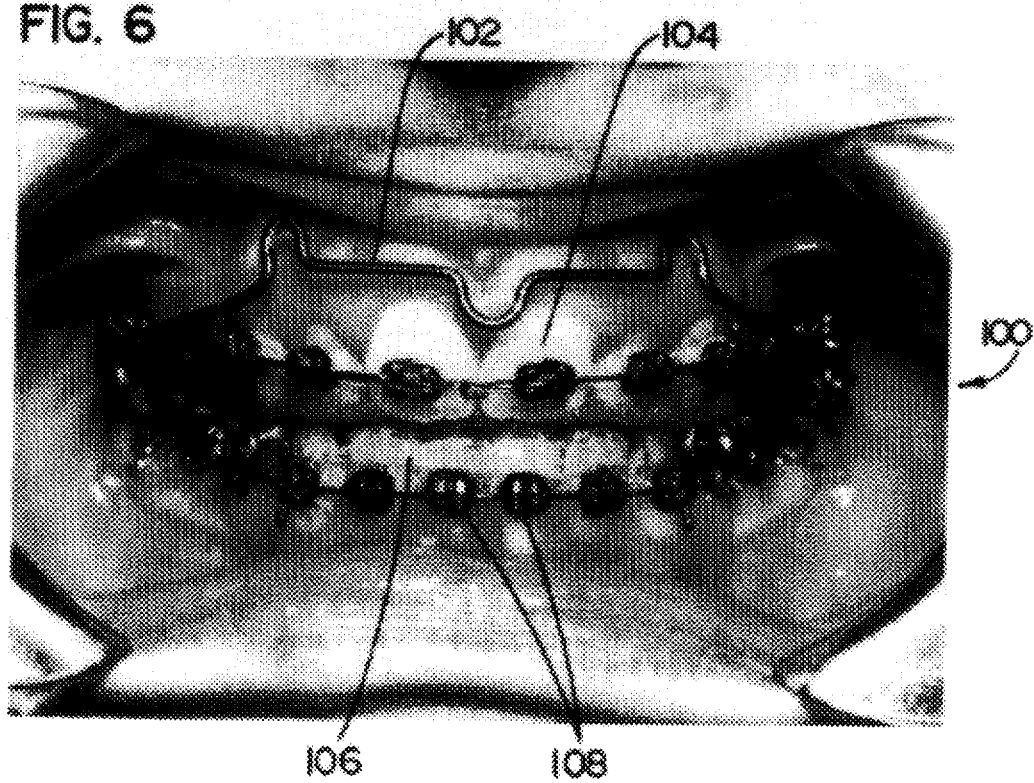
Figure 7:
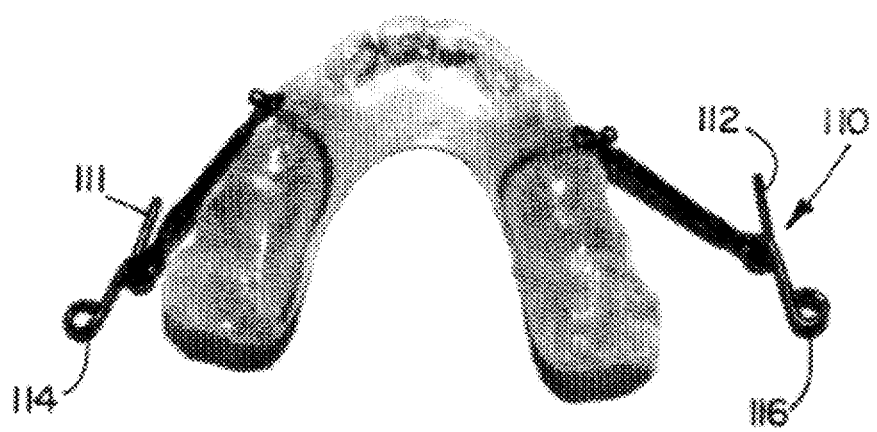
Figure 8:
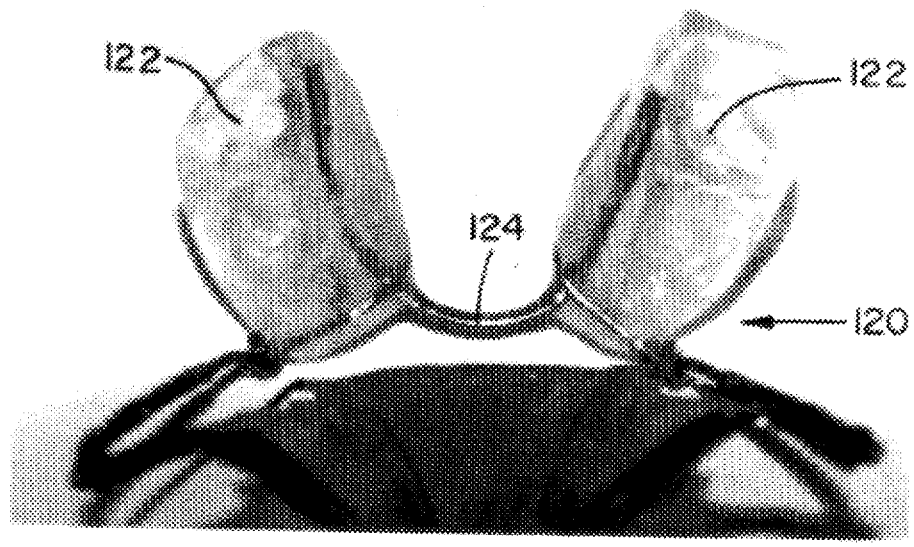
Figure 9:
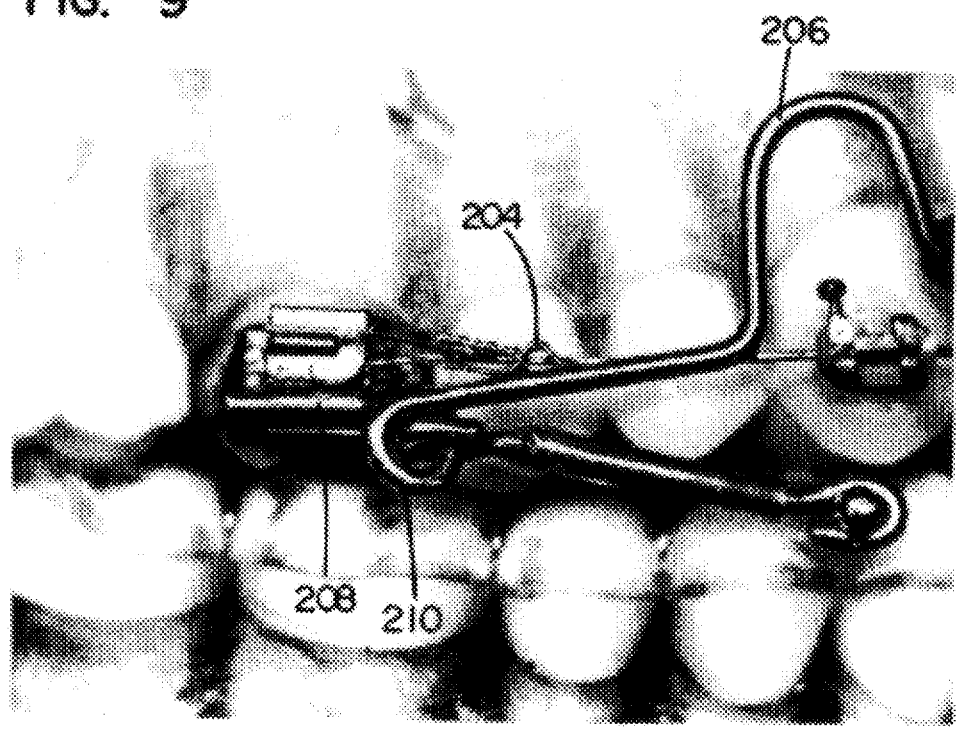

FIG. 2 is a perspective view of a functional regulating device similar to that shown in FIG. 1;

FIG. 3 is a side view of a connector bar, which is a crimped pin and tube arrangement, being adjusted according to the principles of the present invention;

FIG. 4 is a side view of an alternative embodiment of the functional regulating device according to the principles of the present invention, wherein the device is shown on a model and includes a Hawley-type retainer;

FIG. 5 is a top view of a Hawley-type retainer for use in the functional regulating device according to principles of the present invention;

FIG. 6 is a front view of a functional regulating device according to the principles of the present invention, wherein the device is shown being used in combination with braces;

FIG. 7 is a perspective view of an alternative embodiment of a functional regulating device according to the principles of the present invention where pins are provided to fit into headgear tubes;

FIG. 8 is a perspective view of a functional regulating device according to the principles of the present invention having a posterior bite bloc and a lingual bar;

FIG. 9 is a side view of an alternative embodiment of the functional regulating device of the present invention where the device is wired into headgear tubes.

DETAILED DESCRIPTION OF THE INVENTION

The preferred embodiment of the invention will be described in detail with reference to the drawings, wherein like reference numerals represent like parts and assemblies throughout the several views. Reference to the preferred embodiment does not limit the scope of the invention, which is limited only by the scope of the claims attached hereto.

Referring to FIG. 1, an embodiment of the functional regulating device according to the principles of the present invention is shown at 10 in a patient's mouth. The functional regulating device 10 can be used for a class II relationship and includes a lower jaw attachment region 12, an upper jaw attachment region 14, and connecting regions 16, 18 for connecting the lower jaw attachment region 12 and the upper jaw attachment region 14 together to provide a hinge action. It is to be understood that the hinge action is intended to describe a movement between two planes or objects separated by two fixed length bars, wherein each bar has a first end hingedly connected to one plane or object and a second end hingedly connected to the other plane or object. In particular, it is meant to describe the movement of the functional regulating device 10 when the upper and lower jaws provide a biting and releasing motion or a talking motion. The particulars of the hinge action will become more apparent from the following description of the invention.

The functional regulating device of the invention can be assembled in a patient's mouth from several parts. Upon assembly, it can be permanently held together but can be detachable from the patient's mouth. It should be understood that in the context of the present invention, the description of an article or apparatus being "detachable" means that it can be removed and replaced by the patient without the help or assistance of a health care professional. In particular, it can be conveniently removed and replaced several times a day for hygiene and/or cosmetic reasons without detrimentally effecting its usefulness. At times, this feature of the device may be referred to as "releasable attachment." The description of an article or apparatus being "permanent" refers to the need for an orthodontist, dentist or other qualified health care professional for its application, removal, and adjustment. Generally, the permanency of an article or apparatus in a patient's mouth can be reflected by its being bonded in place or by the need for special tools for removal. The permanency of components joined together can be demonstrated by the need for special tools to provide proper adjustment.

The lower jaw attachment region 12 can be fit to a patient's lower jaw and be detachable therefrom. Preferably, it sufficiently fits onto the lower jaw so that it remains in place when used as part of the apparatus 10 during the patient's normal motion of the jaw while talking. The lower attachment region 12 is preferably a lower jaw splint 20 which is a detachable full coverage splint, custom molded to fit or snap onto the lower row of teeth. The splint 20 can be made of any biologically safe material which has sufficient strength to withstand or resist mastication. Preferably, an acrylic material can be used. A splint which can be used in the invention includes splints which are commonly used in the dental industry. Exemplary splints are described in Proffit, William R., *Contemporary Orthodontics*, copyright 1986 by the C. V. Mosby Company, which is incorporated herein by reference.

The lower jaw splint 20 includes axles 22, 24 embedded therein and providing a rotatable connection for the connecting regions 16, 18. The axles 22, 24 are made from 0.040 wire but can be made from larger diameter wire to provide increased strength. As shown in FIG. 2, the axles 22, 24 are provided in the lower jaw splint 20 at a position distal to the cuspid. It is desirable to provide the axles 22, 24 as far forward as possible while retaining sufficient hinge action. It is noted that if the axles are too far forward, teeth may interfere with the hinge action of the functional regulating device 10.

The upper jaw attachment region 14 can be releasably attached to a patient's upper jaw or to fixtures permanently attached to the patient's upper jaw. It is to be understood that the part of the functional regulating device which provides the releasable attachment can be called an anchor. As discussed above, being releasably attached means that the region 14 can be removed and attached by the patient. As a preferred embodiment of the anchor, the upper jaw attachment region 14 includes pins 28, 30 which can be inserted into the head gear tubes on fixed molar bands 32, 34 located on the patient's molars. It is common for conventional head gear tubes welded on molar bands to be located on the first molar or the second molar. It has been found that inserting the pins 28, 30 into the head gear tubes on fixed molar bands 32, 34 provides for sufficient hinge action.

A more detailed view of the pin 30 is shown in FIG. 2. Loops 36, 38 are included to provide a rotatable connection for the connecting regions 16, 18 so that the functional regulating device 10 can have a hinge action. In the embodiment shown, the pins 28, 30 are part of the lip bumper 37 which, because of the action of the lip muscles, provides a source for keeping the pins 28, 30 inserted into the bands 32, 34. It is additionally understood that the action of the muscles in the lower jaw, which are under tension, have a tendency to retract back to the relaxed state which provides a further source for keeping the pins 28, 30 inserted into the bands 32, 34. The lip bumper 37 is 0.045 wire and the loops 36, 38 are mesial to the headgear tube on fixed molar bands 32, 34. It should be appreciated that the lip bumper 37 helps prevent the molars from moving too far back.

The connecting regions 16, 18 are provided to hold the lower jaw attachment region 12 and the upper jaw attachment region 14 together. The connecting regions 16, 18 are shown as connector bars 40, 42 having fixed lengths determined to provide a desired hinge action when attached to the lower attachment region 12 and the upper attachment region 14. The connector bars 40, 42 are crimped pins and tubes which are non-telescoping. This means that, during normal use, the crimped pins and tubes do not slide relative to each other, and the lengths of the connector bars remains fixed. However, it may be possible for the doctor to use special tools to adjust the length during an office visit. Advantageously, the length can be adjusted in a matter of a few minutes while the patient is wearing the functional regulating device. This may be desirable when progressively treating overjet as would be understood by one skilled in the art. For example, rather than trying to reduce the overjet at once, it may be desirable to gradually increase the length of the connector bars to gradually adjust the jaw. This may be important if the overjet is too great (i.e., greater than 10 mm), or if the teeth are concurrently being adjusted.

The functional regulating device 10 can be prepared by providing a lower jaw splint 20 which fits the patient's lower teeth, and an upper jaw attachment region 14 or anchor which fits into the patient's head gear tubes 36, 38. The connector bars 40, 42, provided as pin and tubes, are permanently connected to the axles 22, 24 and permanently connected to the loops 36, 38. At this point, the lengths of the pins and tubes are estimated and are capable of telescoping. When the device is inserted into the patients mouth, the pins and tubes are adjusted until a desired length is provided. The desired length can be referred to as the "predetermined length." At the desired length, the tubes are crimped to prevent the pins from sliding therein. In a preferred arrangement, the pin is a 0.045 wire and is inserted in a 0.045 ID tube. It has been found that this pin and tube size provides sufficient structural support while providing minimum weight and/or bulk.

In general, the length of the connector bars is selected to provide sufficient hinge action, and should allow a patient's mouth to open and close for talking. It is not generally necessary for the device to open wide enough for eating because the device is designed to be easily removable, and can be removed for meals. If the patient's mouth opens too far, the functional regulating device of the present invention will detach but can easily be reattached. It has been found that the functional regulating device of the present invention can be sufficient to provide an opening adequate for speech without being dislodged. It should be understood, however, that in an alternative embodiment of the invention, the functional regulating device can be permanently attached. This may be desirable for a short period, such as one or two months, to coerce compliance. In such a case, however, the degree of hinge can be determined to provide for increased jaw movement. Generally, the need for permanently attaching the device should be fairly infrequent, and for only a short period which is followed by detachable use of the device.

Advantageously, the crimped pin and tube arrangements can be adjusted. As shown in FIG. 3, pliers 45, 46 can be used to pry against each other to further separate the pin 47 and the tube 48. The tube 48 can then be re-crimped once the desired predetermined length is achieved. To provide additional security against slippage or telescoping-type movement, the tube 48 can be crushed behind the pin to further ensure that it will not move into the sleeve. It should be appreciated that this operation can be performed in a patient's mouth.

Now referring to FIGS. 4 and 5, an alternative embodiment of the present invention is provided by functional regulating device 50. As shown, a connector bar 52 is provided with an adjustment loop 54 which provides for altering the length of the connector bar 52. It should be appreciated that this type of connector bar can be used in place of the pin and tube arrangement described above, and that the design and placement of the adjustment loop can be altered. It has been found that the connector bar 52 can be made of 0.045 wire. Of course, the wire should be sufficient to function properly at this location and retain sufficient rigidity and resistance to bending, and can be increased in diameter to 0.050 or 0.055 wire. In addition, the functional regulating device 50 can include a splint 51 and ball clasp 53, similar to that described above.

The functional regulating device 50 additionally includes a Hawley-type retainer 56 as an embodiment of the anchor for releasably attaching the device to the upper jaw. Hawley-type retainers are well known to those skilled in the art. They are commonly used to fit onto a patient's upper jaw after braces have been removed. The retainers are designed to be detachable by the patient. According to the present invention, the retainer 56 can be modified to include axles 58, 59 which extend into and are embedded in the mouth plate 60. The axles 58, 59 include axles 61, 62 to provide a rotatable mount for the connector bars, and sleeves 64, 66 which can provide additional support. The axles can be made of 0.040 wire and the sleeves can be made of 0.040 ID sleeve to provide added strength and to limit the lateral movement of the connector bars. As discussed above, the wire diameter can be increased to provide additional strength. As can be seen in FIG. 5, gaps 67, 68 can be provided outside of the sleeves 64, 66. To provide further support, a reinforcing resin 70 can be placed around the axles and the labial bow 72 to provide additional support and reduce breakage. The reinforcing resin can be any material which sufficiently supports the axle. Preferably, the reinforcing resin is a material which can be applied by a doctor in his/her office or while the functional regulating device is in the patient's mouth, and which will cure quickly. Exemplary materials include thermoform resins, cold cure acrylics, light cure acrylics, and the like.

It is an advantage of the functional regulating device of the present invention that it can be easily fabricated and repaired. In particular, the components of the functional regulating device are commonly available to dentists, and can be modified and assembled according to the teachings of the invention. In addition, it can be easily adjusted at chair side by a doctor or health care professional during an examination. The invention can be practiced without mounting models in an articulator, taking a construction bite or a facebow transfer. It should be appreciated, however, that when a Hawley retainer is used, upper and lower impressions can be poured which is normally done for fabricating Hawley retainers.

If the splint or the Hawley retainer of the functional regulating device is damaged, it can easily be repaired with cold cure acrylic. If damage is too extensive for repair, the broken part can be easily be replaced without the need for mounting models.

The functional regulating device can be advanced in increments for large overjets or all at once as would be apparent to doctors and other appropriate health care professionals.

Many types of lip bumper can be used in the functional regulating device of the present invention. It should be kept in mind, however, that the lip bumper should be capable of advancement as the molars start to distalize. This will prevent the bumper from impinging on the gingival tissue in the incisor area. Headgear can be worn as an alternative to the lip bumper, or in combination with the Hawley-type retainer.

If desired, the functional regulating device can be used with full fixed bonded appliances or braces. As shown in FIG. 6, a functional regulating device 100 having a lip bumper 102 is shown in use with braces 104. Some modification may be necessary, such as trimming the splint 106 above the brackets 108 to provide a better fit. If desired, the lip bumper 102 can be removed and only the pins that fit in the headgear tubes retained. Such a device 110 is shown in FIG. 7 where pins 111, 112 are provided and lip bumper loops 114, 116 are included for attachment of a lip bumper thereto. It should be understood, however, that this design may be more difficult for some patients to insert. Also, the expansion capability may be diminished and there may be a tendency for the upper molars to rotate mesio-buccally. The reason for this is that the force on the molars (having molar tubes which receive the pins 111, 112) causes them to move back and/or rotate mesial-buccally.

As shown in FIG. 8, a functional regulating device 120 can be provided with a posterior bite bloc 122 when the patient exhibits a steep mandibular plane. This can be done without incorporating the lower incisors by use of a lingual bar 124. The labial bow on the upper unit can be modified to eliminate the upper incisors, if desired.

It should be appreciated that functional regulating device of the invention can incorporate auxiliaries, such as sagittal screws, finger springs, buccal shields, palatal expansion screws, and the like. It is generally desirable for the device to be as simple as possible.

As discussed above, in extreme circumstances of poor compliance, the functional regulating device can be permanently wired to the headgear tubes as shown in FIG. 10. In this case, an eyelet 204 can be welded to the bumper 206, and wired to the headgear tube 208. It has been found to be undesirable to use the loop 210 in the 0.045 bumper wire as a tie back since the force of the device has a tendency to break the ligature wire. Special attention to oral hygiene and more frequent visits are necessary in these cases.

An advantage of the functional regulating device of the invention is that it can be implemented gradually during a break-in period, then worn continuously and finally periodically again during a tapering or gradual reduction period. Patients wearing the functional regulating device according to the principles of the present invention may begin with about 8 hours a day of use during the first week to become accustomed to speaking with it in place. During the second week of use, the patients may wear the functional regulating device all day, including while at school, but should not wear it to bed. By the third week, the patients should wear the functional regulating device 24 hours per day, removing it only to eat and for contact sports. It has been found that if patients begin wearing the functional regulating device to bed without a break-in period in which to get accustomed to the device, it may be occasionally removed during sleep.

Patients not having problems with their device may wish to consult their health care professional at about eight week intervals or less. It has been found that when used properly, the functional regulating device of the present invention should provide a steady decrease in overjet of about 1 mm per 8 week period. Greater amounts of improvement are often observed during the beginning of use.

Once the overjet is reduced to about 1-2 mm, the usage or wear time of the functional regulating device may be reduced gradually. If the overjet returns, however, the usage or wear time of the functional regulating device can be increased. Of course, the above protocol depends on the growth stage of the patient, and may vary with individual patients. Accordingly, the treatment protocol should be determined by doctors or other appropriate health care professionals.

It should additionally be appreciated that the functional regulating device of the present invention can be used with class II orthognathic surgery cases that show any sign of relapse after band removal. For example, it has been found acceptable for use for up to 12 months as a retainer to assist stability during this unpredictable adaption period. In addition, the functional regulating device of the invention can be used to treat class III relationship. One skilled in the art would understand how the specific embodiment described herein can be modified for such treatment. In particular, it should be appreciated that the position of the connector bars could be reversed.

While the invention has been described in conjunction with specific embodiments thereof, it is evident that different alternatives, modifications, variations, and uses will be apparent to those skilled in the art in view of the foregoing description. Accordingly, the invention is not limited to these embodiments or the use of elements having specific configurations and shapes as presented herein.

What is claimed is:

1. A functional regulating device for adjusting a bite of a jaw having an upper row of teeth and a lower row of teeth, said functional regulating device comprising:

(a) lower jaw splint constructed and arranged to fit onto the lower row of teeth and be detachable therefrom;

(b) anchor constructed and arranged to attach to the upper row of teeth and be detachable therefrom; and (c) first and second opposed connector bars, each connector bar having a first end and a second end and constructed and arranged to provide predetermined fixed lengths and non-telescoping action when inserted into a jaw, wherein the first ends of said connector bars are permanently connectable to said lower jaw splint, said second ends of the connector bars are permanently connectable to said anchor, said device provides a hinge action when inserted into a patient's mouth, and said connector bars are pin tube arrangements crimped to provide predetermined fixed lengths and non-telescoping rigid members.

2. The functional regulating device according to claim 1, wherein said first connector bar is constructed and arranged for placement on a right side of a patient's jaw, and said second connector bar is constructed and arranged for placement on a left side of a patient's jaw.

3. The functional regulating device according to claim 1, wherein said anchor comprises a lip bumper constructed and arranged to fit in permanently attached head gear tubes on molar bands.

4. The functional regulating device according to claim 1, wherein said anchor comprises a retainer.

5. The functional regulating device according to claim 1, wherein said anchor comprises pins constructed and arranged to fit in permanently attached head gear tubes on molar bands.

6. A functional regulating device for adjusting a bite of a jaw having an upper row of teeth and a lower row of teeth, said functional regulating device comprising:

(a) lower jaw splint constructed and arranged to fit onto the lower row of teeth and be detachable therefrom;

(b) anchor constructed and arranged to attach to the upper row of teeth and be detachable therefrom; and (c) first and second opposed connector bars, each connector bar having a first end and a second end and constructed and arranged to provide predetermined fixed lengths and non-telescoping action when inserted into a jaw, wherein the first ends of said connector bars are permanently connectable to said lower jaw splint, said second ends of the connector bars are permanently connectable to said anchor, said device provides a hinge action when inserted into a patient's mouth, and said connector bars are rigid wires each having an adjustment loop for adjusting the predetermined fixed lengths.

7. The functional regulating device according to claim 6, wherein said first connector bar is constructed and arranged for placement on a right side of a patient's jaw, and said second connector bar is constructed and arranged for placement on a left side of a patient's jaw.

8. The functional regulating device according to claim 6, wherein said anchor comprises a lip bumper constructed and arranged to fit in permanently attached head gear tubes on molar bands.

9. The functional regulating device according to claim 6, wherein said anchor comprises a retainer.

10. The functional regulating device according to claim 6, wherein said anchor comprises pins constructed and arranged to fit in permanently attached head gear tubes on molar bands.

11. A method for treating malocclusion in a patient, said method comprising steps of:

(a) applying a functional regulating device to a patient suffering from malocclusion, said functional regulating device comprising:

(i) lower jaw splint constructed and arranged to fit onto the lower row of teeth and be detachable therefrom;

(ii) anchor constructed and arranged to attach to the upper row of teeth and be detachable therefrom; and (iii) first and second opposed connector bars, each connector bar having a first end and a second end and constructed and arranged to provide predetermined fixed lengths and non-telescoping action when inserted into a jaw, wherein the first ends of said connector bars are permanently connectable to said lower jaw splint, the second ends of said connector bars are permanently connectable to said anchor, said device provides a hinge action in a patient's mouth during normal talking motion, and said connector bars are pin and tube arrangements crimped to provide predetermined fixed lengths and non-telescoping rigid members.

12. The method for treating malocclusion in a patient according to claim 11, further comprising adjusting the length of the connector bars.

13. The method for treating malocclusion according to claim 11, wherein said step of adjusting occurs while the patient is wearing the functional regulating device.

14. A method for treating malocclusion in a patient, said method comprising steps of:

(a) applying a functional regulating device to a patient suffering from malocclusion, said functional regulating device comprising:

(i) lower jaw splint constructed and arranged to fit onto the lower row of teeth and be detachable therefrom;

(ii) anchor constructed and arranged to attach to the upper row of teeth and be detachable therefrom; and (iii) first and second opposed connector bars, each connector bar having a first end and a second end and constructed and arranged to provide predetermined fixed lengths and non-telescoping action when inserted into a jaw, wherein the first ends of said connector bars are permanently connectable to said lower jaw splint, the second ends of said connector bars are permanently connectable to said anchor, said device provides a hinge action in a patient's mouth during normal talking motion, and said connector bars are rigid wires each having an adjustment loop for adjusting the predetermined fixed lengths.

15. The method for treating malocclusion in a patient according to claim 14, further comprising adjusting the length of the connector bars.

16. The method for treating malocclusion according to claim 15, wherein said step of adjusting occurs while the patient is wearing the functional regulating device.

* * * * *

UNITED STATES PATENT AND TRADEMARK OFFICE
CERTIFICATE OF CORRECTION

PATENT NO. : 5,697,781
DATED : December 16, 1997
INVENTOR(S) : Ellingson

It is certified that error appears in the above-identified patent and that said Letters Patent is hereby corrected as shown below:

On the title page, item [56]
  "Other Publications": "The Herbst Appliance" should read ---The Bionator Appliance---

Signed and Sealed this

Fifteenth Day of September, 1998

Attest:

BRUCE LEHMAN

Attesting Officer

Commissioner of Patents and Trademarks